(12) United States Patent
Creekmore et al.

(10) Patent No.: US 6,548,513 B1
(45) Date of Patent: *Apr. 15, 2003

(54) PHARMACEUTICAL COMPOSITIONS

(75) Inventors: Joseph R Creekmore, Wilmington, DE (US); Norman A. Wiggins, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/633,114

(22) Filed: Aug. 4, 2000

(30) Foreign Application Priority Data

Jan. 26, 2000 (GB) .............................. 0001621

(51) Int. Cl.⁷ ..................... A61K 31/505; C07D 239/34
(52) U.S. Cl. ...................... 514/275; 514/256; 514/557; 544/322
(58) Field of Search ................. 424/464, 465, 424/489, 488; 544/322; 514/183, 184, 275, 86, 524, 256, 557

(56) References Cited

U.S. PATENT DOCUMENTS

| 4,743,450 A | | 5/1988 | Harris et al. | |
| 5,260,440 A | * | 11/1993 | Harai et al. | 544/322 |
| 5,356,896 A | | 10/1994 | Kabadi et al. | |
| 5,665,881 A | * | 9/1997 | Inoue et al. | 546/170 |
| 5,686,104 A | | 11/1997 | Mills et al. | |
| 6,150,410 A | | 11/2000 | Engh et al. | |
| 6,316,460 B1 | * | 11/2001 | Creekmore et al. | 514/275 |

FOREIGN PATENT DOCUMENTS

| EP | 0 336 298 | 3/1988 |
| EP | 0 380 021 | 8/1990 |
| EP | 0 398 619 A2 | 11/1990 |
| EP | 0 521 471 | 11/1990 |
| EP | 0 475 482 A1 | 3/1992 |
| EP | 0 521 471 A1 | 1/1993 |
| GB | 653026 | 5/1951 |
| GB | 2 262 229 | 6/1993 |
| WO | 97/23200 | 7/1997 |
| WO | WO 99/62560 | 12/1999 |
| WO | 00/35425 | 6/2000 |
| WO | WO 00/42024 | 7/2000 |
| WO | WO 00/45817 | 8/2000 |
| WO | WO 00/45818 | 8/2000 |
| WO | WO 00/45819 | 8/2000 |

OTHER PUBLICATIONS

Remington's Pharmaceutical Sciences, 13th Ed., 1965, left –hand column, lines 25–27.

Watanabe et al., "Synthesis and Biological Activity of Methanesulfonamide Pyrimidine– and N–Methanesulfonyl Pyrrole–Substituted 3,5–Dihydroxy–6–heptenoates, a Novel Seriesl fo HMG–CoA Reductase Inhibitors", Bioorganic & Medicinal Chemistry, vol. 5, No. 2, 1997, pp. 437–444.

Creekmore et al., Appln. Ser. No. 09/633,064 Aug. 4, 2000.

* cited by examiner

Primary Examiner—Deborah D. Carr
(74) Attorney, Agent, or Firm—Morgan, Lewis & Bockius LLP

(57) ABSTRACT

The present invention relates to pharmaceutical compositions and more particularly to a pharmaceutical composition containing (E)-7-[4-(4-fluorophenyl)-6-isopropyl-2-[methyl(methylsulfonyl)amino]pyrimidin-5-yl]-(3R, 5S)-3,5-dihydroxyhept-6-enoic acid or a pharmaceutically-acceptable salt thereof as the active ingredient and an inorganic salt in which the cation is multivalent.

19 Claims, No Drawings

PHARMACEUTICAL COMPOSITIONS

The present invention relates to pharmaceutical compositions and more particularly to a pharmaceutical composition containing (E)-7-[4-(4-fluorophenyl)-6-isopropyl-2-[methyl(methylsulfonyl)amino]pyrimidin-5-yl]-(3R, 5S)-3,5-dihydroxyhept-6-enoic acid or a pharmaceutically-acceptable salt thereof (and referred to hereinafter as "the Agent"). In particular the sodium and calcium salts, and especially the calcium salt, bis[(E)-7-[4-(4-fluorophenyl)-6-isopropyl-2-[methyl(methylsulfonyl)amino]pyrimidin-5-yl]-(3R, 5S)-3,5-dihydroxyhept-6-enoic acid]calcium salt (shown as Formula I below).

The Agent is disclosed as an inhibitor of 3-hydroxy-3-methylglutaryl CoA reductasent in (HMG CoA reductase) in European Patent Application, Publication No. 0521471 and in Bioorganic and Medicinal Chemistry, (1997), 5(2), 437–444 and is useful in the treatment of hypercholesterolemia, hyperlipidproteinemia and atherosclerosis.

A problem associated with the Agent is that it is particularly sensitive to degradation under certain conditions. The major degradation products formed are the corresponding (3R, 5S) lactone (hereinafter referred to as "the lactone") and an oxidation product (hereinafter referred to as "B2") in which the hydroxy group adjacent to the carbon-carbon double bond is oxidised to a ketone functionality. The potential for significant degradation of the Agent makes it difficult to formulate and provide a pharmaceutical composition with acceptable storage life for a marketed product.

Pharmaceutical formulations of certain 7-substituted-3,5-dihydroxy-6-heptenoic acid salts, which are HMG CoA reductase inhibitors, are disclosed in UK Patent 2 262 229, and that they are sensitive to pH degradation. These formulations require the presence of an alkaline medium (such as a carbonate or bicarbonate) capable of imparting a pH of at least 8 to an aqueous solution or dispersion of the composition.

However, we have found that for the Agent it is not sufficient to improve stability by solely controlling pH in the formulation. We have found that with the Agent stability is improved by selection of an inorganic salt to be added to the composition which contains one or more multivalent inorganic cations. Whilst not wishing to be bound by theory we believe that the multivalent inorganic cation stabilises the structure of the Agent and makes it less susceptible to oxidation and/or lactonization.

We present as a feature of the invention
(1) A pharmaceutical composition comprising the Agent as an active ingredient and an inorganic salt in which the cation is multivalent.
(2) The use of an inorganic salt in which the cation is multivalent as a stabilising agent in a pharmaceutical composition comprising the Agent.

Preferred features of the invention are:
(1) wherein the Agent is present in the composition is more than 5 mg, preferably more than 10 mg. Excluded compositions are those wherein the Agent is present at 1 mg, 2 mg, 5 mg and 10 mg. Preferred compositions are those where the amount of Agent is 20 mg, 40 mg or 80 mg.
(2) wherein the stabilising compound is not synthetic hydrotalcite.
(3) the pharmaceutical composition formed is a tablet or a powder.

Preferably the pharmaceutical composition of the invention is a tablet.

The multivalent cation found in the inorganic salt may be selected from the following, calcium, magnesium, zinc, aluminium and iron or a mixture thereof. Preferred multivalent cations are calcium, aluminium and magnesium or a mixture thereof. Especially preferred multivalent cations are aluminium and magnesium or a mixture thereof.

The counter anion in the inorganic salt may be selected from a phosphate, a carbonate, a silicate, an oxide and a metasilicate. Preferred counter anions are selected from a carbonate, a silicate, an oxide and a metasilicate. Especially preferred counter anions are selected from a silicate, an oxide or a metasilicate.

Individual aspects of the invention include an inorganic salt comprising a multivalent cation selected from any of the above and a counter anion also selected from any of the above.

Preferred inorganic salts for use in the present invention are; aluminium magnesium metasilicate (Neusolin™, Fuji Chemical Industry Limited), dibasic or tribasic calcium phosphate, tribasic magnesium phosphate and tribasic aluminium phosphate. Aluminium magnesium metasilicate and tribasic calcium phosphate are especially preferred.

It is also preferable that such a composition has a good flow rate to assist processing into unit dosage forms for oral administration, for example into tablets, and good disintegration and dissolution characteristics when processed into tablets for oral administration, which tablets can be in different dosage strengths.

The ratio of inorganic salt to Agent in the pharmaceutical composition is, for example, within the range of 1:80 to 50:1 by weight, for example 1:50 to 50:1 by weight, such as 1:10 to 10:1 by weight, and more particularly 1:5 to 10:1 by weight.

Preferably the pharmaceutical composition of the invention is formulated into an oral dosage form, such as a tablet. Accordingly a further aspect of the invention comprises a pharmaceutical composition comprising the Agent, an inorganic salt in which the cation is multivalent, and one or more fillers, binders, disintegrants or lubricants. A still further aspect of the invention relates to a pharmaceutical composition for oral administration comprising the Agent, one or more fillers, one or more binders, one or more disintegrants, one or more lubricants and an inorganic salt in which the cation is multivalent.

Suitable fillers include, for example, lactose, sugar, starches, modified starches, mannitol, sorbitol, inorganic salts, cellulose derivatives (e.g. microcrystalline cellulose, cellulose), calcium sulfate, xylitol and lactitol.

Suitable binders include, for example, polyvinylpyrrolidone, lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatin and sodium alginate.

Suitable disintegrants include, for example, crosscarmellose sodium, crospovidone, polyvinylpyrrolidone, sodium starch glycollate, corn starch, microcrystalline cellulose, hydroxypropyl methylcellulose and hydroxypropyl cellulose.

Suitable lubricants include, for example, magnesium stearate, stearic acid, palmitic acid, calcium stearate, talc, carnauba wax, hydrogenated vegetable oils, mineral oil, polyethylene glycols and sodium stearyl fumarate.

Additional conventional excipients which may be added include preservatives, stabilisers, anti-oxidants, silica flow conditioners, antiadherents or glidants.

Other suitable fillers, binders, disintegrants, lubricants and additional excipients which may be used are described in *Handbook of Pharmaceutical Excipients*, 2$^{nd}$ Edition, American Pharmaceutical Association; *The Theory and Practice of Industrial Pharmacy*,2$^{nd}$ Edition, Lachman, Leon, 1976; *Pharmaceutical Dosage Forms: Tablets Volume* 1, 2$^{nd}$ Edition, Lieberman, Hebert A., et al, 1989; *Modern Pharmaceutics*, Banker, Gilbert and Rhodes, Christopher T, 1979; and *Remington's Pharmaceutical Sciences*, 15$^{th}$ Edition, 1975.

Typically the Agent will be present in an amount within the range of 1 to 50%, for example 1 to 25%, such as 1 to 20%, and particularly 5 to 18% by weight.

Typically the inorganic salt, such as tribasic calcium phosphate, will be present in an amount within the range of 1 to 25%, for example 1 to 20%, such as 5 to 18% by weight.

Typically one or more fillers will be present in an amount 30 to 90% by weight.

Typically one or more binders will be present in an amount 2 to 90% by weight.

Typically one or more disintegrants will be present in an amount 2 to 10%, and especially 4 to 6% by weight.

It will be appreciated that a particular excipient may act as both a binder and a filler, or as a binder, a filler and a disintegrant. Typically the combined amount of filler, binder and disintegrant comprises, for example, 70 to 90% by weight of the composition.

Typically one or more lubricants will be present in an amount 0.5 to 3%, and especially 1 to 2% by weight.

The pharmaceutical composition of the invention may be prepared, using standard techniques and manufacturing processes generally known in the art, for example by dry blending the components. For example, the Agent and an inorganic salt in which the cation is multivalent, one or more fillers, one or more binders and one or more disintegrants, as well as other additional excipients if desired are blended together. The components of the blend prior to blending, or the blend itself, may be passed through a mesh screen, for example a 400–700 μm mesh screen. A lubricant, which may also be screened, is then added to the blend and blending continued until a homogeneous mixture is obtained. The mixture is then compressed into tablets. Alternatively, a wet granulation technique can be employed. For example, the Agent and an inorganic salt in which the cation is multivalent, one or more fillers, one or more binders and a portion of a disintegrant, as well as other additional excipients if desired, are blended together, for example by using a granulator, and the powder blend is granulated with a small volume of purified water. The granulate is dried and passed though a mill. The remainder of the disintegrant and a lubricant are added to the milled granulation and after blending the resultant homogeneous mixture is compressed into tablets. It will be appreciated that modifications of the dry blending and wet granulation techniques, including the order of addition of the components and their screening and blending prior to compression into tablets, may be carried out according to principles well known in the art.

A tablet coating may then be applied, for example by spray-coating, with a water-based film coating formulation. The coating may comprise, for example, lactose, hydroxypropyl methylcellulose, triacetin, titanium dioxide and ferric oxides. Coating ingredient combinations are commercially available, such as those described in the Examples hereinafter. The coating may comprise, for example, 0.5 to 10% by weight of the tablet composition, particularly 1 to 6%, and preferably 2 to 3%. Coatings containing ferric oxides are especially preferred as they reduce the rate of formation of photodegradation products of the Agent.

Accordingly we present as a feature of the invention a pharmaceutical composition comprising the Agent, the composition having a ferric oxide light protective coating.

A further aspect of the present invention comprises a method of preparing a stabilised pharmaceutical composition which comprises admixing the Agent with an inorganic salt in which the cation is multivalent. A further aspect of the present invention comprises a method of producing a stabilised pharmaceutical composition which comprises incorporating a inorganic salt in which the cation is multivalent in a pharmaceutical composition containing the Agent.

EXAMPLE 1

| | |
|---|---|
| The Agent | 2.50 mg |
| Tribasic calcium phosphate | 20.0 mg |
| Microcrystalline cellulose | 47.0 mg |
| Lactose monohydrate | 47.0 mg |
| Sodium starch glycollate | 3.00 mg |
| Butylated hydroxytoluene | 0.05 mg |
| Magnesium stearate | 1.00 mg |

The Agent, microcrystalline cellulose, lactose monohydrate, sodium starch glycolate, tribasic calcium phosphate, and butylated hydroxytoluene were blended together for 10 minutes. Magnesium stearate was screened through a #40 mesh (425 μm) screen and added to the blend and blending continued for a further three minutes. The resulting homogeneous mixture was compressed into tablets.

The tablets were stored at 70° C./80% relative humidity for one week. After one week there was found to be only 0.11%w/w of the oxidation product B2 formed and only 0.50%w/w of the lactone.

EXAMPLE 2

| | |
|---|---|
| The Agent | 2.50 mg |
| Povidone | 2.50 mg |
| Tribasic calcium phosphate | 20.0 mg |
| Microcrystalline cellulose | 47.0 mg |
| Mannitol | 47.0 mg |
| Sodium starch glycollate | 3.00 mg |
| Butylated hydroxytoluene | 0.05 mg |
| Magnesium stearate | 1.00 mg |

The Agent, povidone, mannitol, microcrystalline cellulose, butylated hydroxytoluene, tribasic calcium phosphate and sodium starch glycollate (in the amounts given below) were blended for 5 to 60 minutes. Magnesium stearate was screened through a #40 mesh (425 μm) screen and added to the blend and blending continued for a further three minutes. The resulting homogeneous mixture was compressed into tablets. The compressed tablets were coated by spraying with a mixture of hydroxypropyl methylcellulose, polyethylene glycol 400, titanium dioxide and ferric oxide (sold as Spectrablend™ by Warner-Jenkinson)) and water in a coating pan. The weight gain provided by the coating was 1 to 6%w/w, and preferably 2 to 3%w/w.

The tablets were stored at 70° C./180% relative humidity for one week. After one week there was found to be only 0.06%w/w of the oxidation product B2 formed and only 2.22%w/w of the lactone.

EXAMPLE 3

| | |
|---|---|
| The Agent | 2.60 mg |
| Crospovidone | 3.75 mg |
| Tribasic calcium phosphate | 5.66 mg |
| Microcrystalline cellulose | 15.5 mg |
| Lactose monohydrate | 46.5 mg |
| Magnesium stearate | 0.94 mg |

The Agent and crospovidone were blended together for 5 minutes and the blend then passed through a 400–700 μm screen. A small portion of the microcrystalline cellulose was passed through the screen afterwards. The screened material was blended with the other ingredients, excluding the lubricant, for 10 minutes. Magnesium stearate was passed through a #40 mesh (425 μm) screen and added to the blend and the mixture was blended for a further 3 minutes. The resulting homogeneous mixture was compressed into tablets. The compressed tablets were coated by spraying with a mixture of lactose monohydrate, hydroxypropyl methylcellulose, triacetin and ferric oxide (sold as Opadry II™ by Colorcon) and water in a coating pan. The weight gain provided by the coating is 1 to 6%w/w, and preferably 2 to 3%w/w.

The tablets were stored at 70° C./80% relative humidity for one week. After this time only 0.19%w/w of the oxidation product B2 had formed and only 2.71%w/w of the lactone.

EXAMPLE 4

| | |
|---|---|
| The Agent | 2.50 mg |
| Povidone | 2.50 mg |
| Tribasic calcium phosphate | 20.0 mg |
| Microcrystalline cellulose | 34.5 mg |
| Lactose monohydrate | 34.0 mg |
| Sodium starch glycollate | 6.00 mg |
| Magnesium stearate | 1.00 mg |
| Butylated hydroxytoluene | 0.05 mg |

A portion of the tribasic calcium phosphate and butylated hydroxytoluene were blended for 30 seconds in a bag. The Agent, povidone, remainder of the tribasic calcium phosphate, microcrystalline cellulose, lactose monohydrate, tribasic calcium phosphate/butylated hydroxytoluene mixture and a portion of the sodium starch glycolate were blended in a granulator for 30 seconds. The powder blend was granulated with purified water for 1 minute at the addition rate of 70 mg/tablet/minute. The granulation is dried in a fluidized bed drier at 50° C. until the loss on drying is less than 2%w/w. The dried granulation is passed through a mill (e.g. Comil™). The milled granulation and the remainder of the sodium starch glycolate was blended for approximately 5 minutes. Magnesium stearate was screened through a #40 mesh (425 μm) screen and added to the blend and blending continued for a further three minutes. The resulting homogeneous mixture was compressed into tablets.

The tablets were stored at 70° C./180% relative humidity for one week. After this time only 0.23%w/w of the oxidation product B2 had formed and only 0.28%w/w of the lactone.

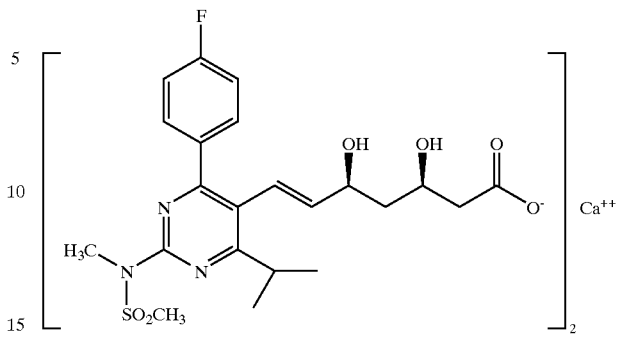

Formula I

What is claimed is:

1. A pharmaceutical composition comprising (E)-7-[4-(4-fluorophenyl)-6-isopropyl-2-[methyl(methylsulfonyl)amino]pyrimidin-5-yl]-(3R, 5S)-3,5-dihydroxyhept-6-enoic acid or a pharmaceutically acceptable salt thereof as the active ingredient and an inorganic salt in which the cation is multivalent, provided that said multivalent cation is not synthetic hydrotalcite.

2. A pharmaceutical composition as claimed in claim 1 wherein the cation of the inorganic salt is selected from calcium, magnesium, zinc, aluminium and iron.

3. A pharmaceutical composition as claimed in claim 1 wherein the inorganic salt is selected from aluminium magnesium metasilicate, tribasic calcium phosphate, tribasic magnesium phosphate and tribasic aluminium phosphate.

4. A pharmaceutical composition as claimed in 3 wherein the inorganic salt is aluminium magnesium metasilicate.

5. A pharmaceutical composition as claimed in claim 1 or claim 2 which is a tablet or powder.

6. A pharmaceutical composition as claimed in claim 1 or claim 2 in which more than 5 mg of active ingredient is present.

7. A pharmaceutical composition as claimed in claim 6 in which more than 10 mg of active ingredient is present.

8. A pharmaceutical composition as claimed in claim 1 or claim 2 wherein the ratio of the inorganic salt to the active ingredient is in the range of 1:80 to 50:1 by weight.

9. A pharmaceutical composition as claimed in claim 1 or claim 2 additionally comprising one or more fillers, binders, disintegrants or lubricants.

10. A pharmaceutical composition as claimed in claim 1 or claim 2 wherein the active ingredient is present in an amount 1 to 50% by weight of the composition.

11. A pharmaceutical composition as claimed in claim 1 or claim 2 wherein the inorganic salt is present in an amount 1 to 50% by weight of the composition.

12. A pharmaceutical composition as claimed in claim 9 wherein the filler is present in an amount 30 to 90% by weight of the composition.

13. A pharmaceutical composition as claimed in claim 10 wherein the binder is present in an amount 2 to 90% by weight of the composition.

14. A pharmaceutical composition as claimed in claim 10 wherein the disintegrant is present in an amount 2 to 10% by weight of the composition.

15. A pharmaceutical composition as claimed in claim 10 wherein the lubricant is present in an amount 0.5 to 3% by weight.

16. A pharmaceutical composition as claimed in claim 1 or claim 2 wherein the active ingredient is the calcium salt of (E)-7-[4-(4-fluorophenyl)-6-isopropyl-2-[methyl (methylsulfonyl)amino]pyrimidin-5-yl]-(3R, 5S)-3,5-dihydroxyhept-6-enoic acid.

17. The method of claim 21 wherein the inorganic salt in which the cation is multivalent is selected from aluminium magnesium metasilicate, tribasic calcium phosphate, tribasic magnesium phosphate and tribasic aluminium phosphate.

18. A method of producing a stabilised pharmaceutical composition which comprises incorporating an inorganic salt in which the cation is multivalent in a pharmaceutical composition containing the compound (E)-7-[4-(4-fluorophenyl)-6-isopropyl2-[methyl(methylsulfonyl)amino]pyrimidin-5-yl]-(3R, 5S)-3,5-dihydroxyhept-6-enoic acid or a pharmaceutically acceptable salt thereof, provided that said multivalent cation is not synthetic hydrotalcite.

19. A method as claimed in claim 18 wherein the inorganic salt in which the cation is multivalent is aluminium magnesium metasilicate.

* * * * *